(12) United States Patent
Subbiah et al.

(10) Patent No.: US 8,774,469 B2
(45) Date of Patent: Jul. 8, 2014

(54) SYSTEM AND METHOD FOR ANALYZING PROPERTIES OF MEAT USING MULTISPECTRAL IMAGING

(75) Inventors: Jeyamkondan Subbiah, Lincoln, NE (US); Chris Richard Calkins, Lincoln, NE (US); Ashok Kumor Samal, Lincoln, NE (US); Govindarajan Konda Naganathan, Lincoln, NE (US)

(73) Assignee: Goldfinch Solutions, LLC, Lincoln, NE (US)

( * ) Notice: Subject to any disclaimer, the term of this patent is extended or adjusted under 35 U.S.C. 154(b) by 372 days.

(21) Appl. No.: 13/143,897

(22) PCT Filed: Jan. 11, 2010

(86) PCT No.: PCT/US2010/020683
§ 371 (c)(1),
(2), (4) Date: Jul. 8, 2011

(87) PCT Pub. No.: WO2010/081116
PCT Pub. Date: Jul. 15, 2010

(65) Prior Publication Data
US 2011/0273558 A1    Nov. 10, 2011

Related U.S. Application Data

(60) Provisional application No. 61/143,783, filed on Jan. 10, 2009.

(51) Int. Cl.
*G06K 9/00*    (2006.01)

(52) U.S. Cl.
USPC ............ 382/110; 348/135; 362/231; 356/303

(58) Field of Classification Search
USPC ............ 382/100, 110, 141, 191, 207; 348/92, 348/135; 356/300, 303; 362/2, 227, 230, 362/231, 293
See application file for complete search history.

(56) References Cited

U.S. PATENT DOCUMENTS

| | | | | |
|---|---|---|---|---|
| 5,339,815 A | * | 8/1994 | Liu et al. | 600/437 |
| 5,576,949 A | * | 11/1996 | Scofield et al. | 702/179 |
| 5,944,598 A | * | 8/1999 | Tong et al. | 452/158 |
| 5,991,028 A | | 11/1999 | Cabib et al. | |
| 6,198,834 B1 | * | 3/2001 | Belk et al. | 382/110 |
| 6,256,409 B1 | | 7/2001 | Wang | |

(Continued)

FOREIGN PATENT DOCUMENTS

WO    WO2009-005828    1/2009

*Primary Examiner* — Anand Bhatnagar
(74) *Attorney, Agent, or Firm* — Hemingway & Hansen, LLP; D. Scott Hemingway

(57) ABSTRACT

A system and method for obtaining multispectral images of fresh meat at predetermined wavelength bands at a first time, subjecting the images to analysis in an image analysis system comprising a computer programmed to perform such analysis, and outputting a forecast of meat tenderness at a later point in time. Predetermined key wavelength bands are pre-correlated with a high degree of prediction of meat tenderness and/or other properties of meat and are used in the multispectral system and method. A system and method for determining the key wavelengths is also disclosed. The multispectral imaging system and method is suitable for use in an industrial setting, such as a meat processing plant. The system and method is useful in a method for determining quality and yield grades at or near the time of imaging in lieu of visual inspection with the unaided human eye, increasing efficiency and objectivity.

51 Claims, 9 Drawing Sheets

(56) References Cited

U.S. PATENT DOCUMENTS

| | | | |
|---|---|---|---|
| 6,563,580 B1 * | 5/2003 | Aignel et al. | 356/300 |
| 6,587,575 B1 * | 7/2003 | Windham et al. | 382/110 |
| 6,615,661 B2 * | 9/2003 | King | 73/602 |
| 6,639,665 B2 | 10/2003 | Poole | |
| 7,190,813 B2 | 3/2007 | Daley et al. | |
| 7,218,775 B2 | 5/2007 | Kokko et al. | |
| 7,263,226 B1 | 8/2007 | Stein | |
| 2008/0123097 A1 | 5/2008 | Muhammed et al. | |
| 2011/0007151 A1 * | 1/2011 | Goldberg | 348/135 |

* cited by examiner

SYSTEM AND METHOD FOR ANALYZING PROPERTIES OF MEAT USING MULTISPECTRAL IMAGING

CROSS REFERENCE TO RELATED APPLICATIONS

This application claims the benefit of U.S. Provisional Application No. 61/143,783, filed Jan. 10, 2009.

STATEMENT REGARDING FEDERALLY SPONSORED RESEARCH OR DEVELOPMENT

Not applicable.

TECHNICAL FIELD OF INVENTION

This invention relates to the field of the meat processing, analysis, and classification.

BACKGROUND OF THE INVENTION

Meat processing, analysis and classification are important so that consumers can obtain quality meat products for consumption and be provided with information about the meat at the point of purchase. The United States is a large producer of beef, pork and other meats. In the United States beef industry, beef grading standards were developed by the United States Department of Agriculture (USDA) to classify carcasses into quality and yield grades. Beef tenderness is an important quality attribute associated with consumer satisfaction. Presently, the USDA grading system is unable to incorporate a direct measure of tenderness because there is no accurate, rapid, nondestructive method for predicting tenderness available to the beef industry. Thus, beef carcasses are not priced on the basis of actual tenderness, creating a lack of incentives for producers to supply a tender product. Similar issues are present with respect to pork and other meat products.

Video image analysis systems have been reported as useful for predicting beef grades. A near-infrared spectroscopy system to predict beef tenderness has also been reported; however, the beef industry has not adopted this technology due to its technological limitations and low accuracy. Categorizing meat cuts by tenderness would enhance economic opportunities for cattle and other livestock producers and processors by improving assessment of beef product quality to meet consumer expectations. Also, it would help the U.S. beef industry maintain or expand its market in the face of increasing competition from other protein sources. Labeling accurate quality factors on the packaging of retail cuts would add value to the products and benefit consumers.

DETAILED DESCRIPTION OF THE INVENTION

Figure 1:
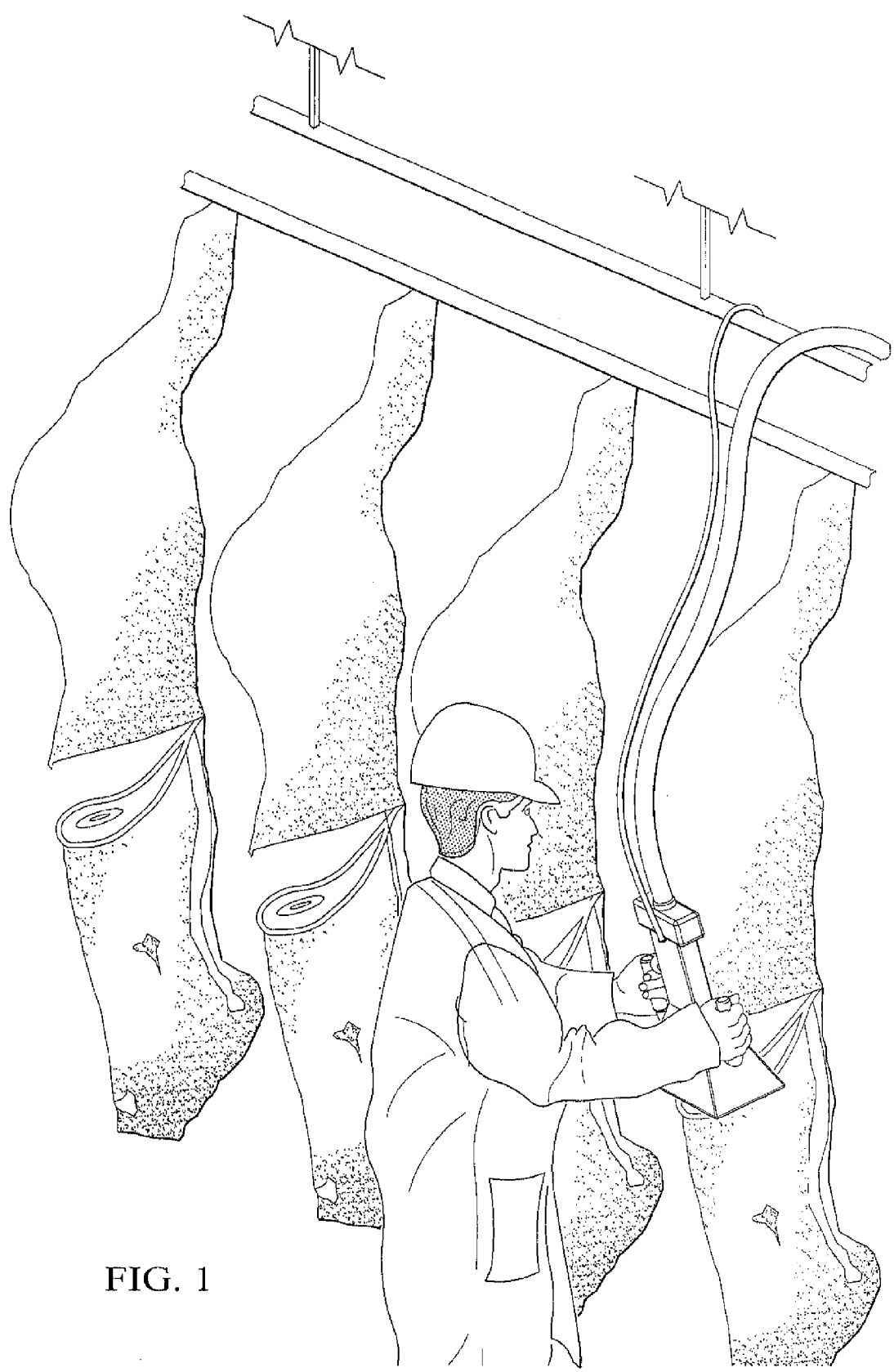
FIG. 1 is an environmental view of an operator utilizing a multispectral image acquisition camera to obtain an image of a portion of a beef carcass.

A system and method is disclosed for non-destructively analyzing fresh meat at a time ($t_0$) whereby a forecast of the tenderness and/or other properties of said meat at a later time ($t_1$) is obtained. Time ($t_0$) is a time occurring post mortem after rigor mortis is complete. Time ($t_1$) is a later time than ($t_0$), the time or date when it is known or estimated that the meat first will be available to a consumer for preparation by cooking. The forecast provides information about the fresh meat product well in advance of time ($t_1$) which data and experience has revealed may be 14 days or more from the date of slaughter. Tenderness generally increases from ($t_0$) to ($t_1$), but heretofore there has been no rapid efficient system or method for forecasting the nature of the increase in tenderness. Since tenderness and/or other desirable attributes of the fresh meat product have value to consumers, employing the system and method of the invention to obtain the forecast of the tenderness and/or other desirable attributes will give meat producers advance information as to the value of the fresh meat product in the marketplace. This will allow producers to price and position the products appropriately.

The system and method may also be used to determine information about said meat at time ($t_0$) in a rapid and objective manner.

The system and method comprises a multispectral imaging system that collects images at predetermined key wavelength bands from raw meat. The multispectral imaging system comprises an image acquisition means such as a specialized camera which captures images from a meat portion at time ($t_0$), a computer programmed to receive said images, extract data from said images, and perform computations on said data, said computations resulting in output of said forecast as to properties of the meat being analyzed at time ($t_0$) for forecast time ($t_1$). Preferably, said multispectral imaging system further comprises an output means to which said computer outputs or displays the results of the computations in a form understandable to a human in need of such data. The computer may optionally be in communication with an archival means such as a database which can store image data and forecasts.

The forecast comprises a prediction of the tenderness and/or other properties of the meat from a selected specimen of meat, such as a portion of a beef side which conventionally undergoes limited analysis by visual inspection. Though the system and method may be useful in a number of settings, it is particularly useful for the meat processing industry. In a preferred embodiment, the system and method is employed in a meat processing plant production line ("on-line" operation) at the same time, just subsequent to, or in place of other evaluations routinely employed voluntarily or mandated by law.

The system and method is also useful in other settings where meat is processed, butchered or packed. Such operations may be highly automated and the multispectral imaging system can be adapted for participation in an automated process. For example, the camera can be mounted on a stand, while cuts of steaks on a conveyor belt move to a position which will permit the camera to acquire a multispectral image from each steak. A computer in communicative relationship with the camera receives said images, extracts data, performs computations, and outputs a forecast of tenderness and/or other properties of each steak.

Another setting for implementation of the system and method of the invention may be by meat marketers and sellers. For example, hand-held units with on-board computers could be used by retail stores, restaurants, and even consumers to assist them in making decisions about the qualities of a meat product.

Figure 2:
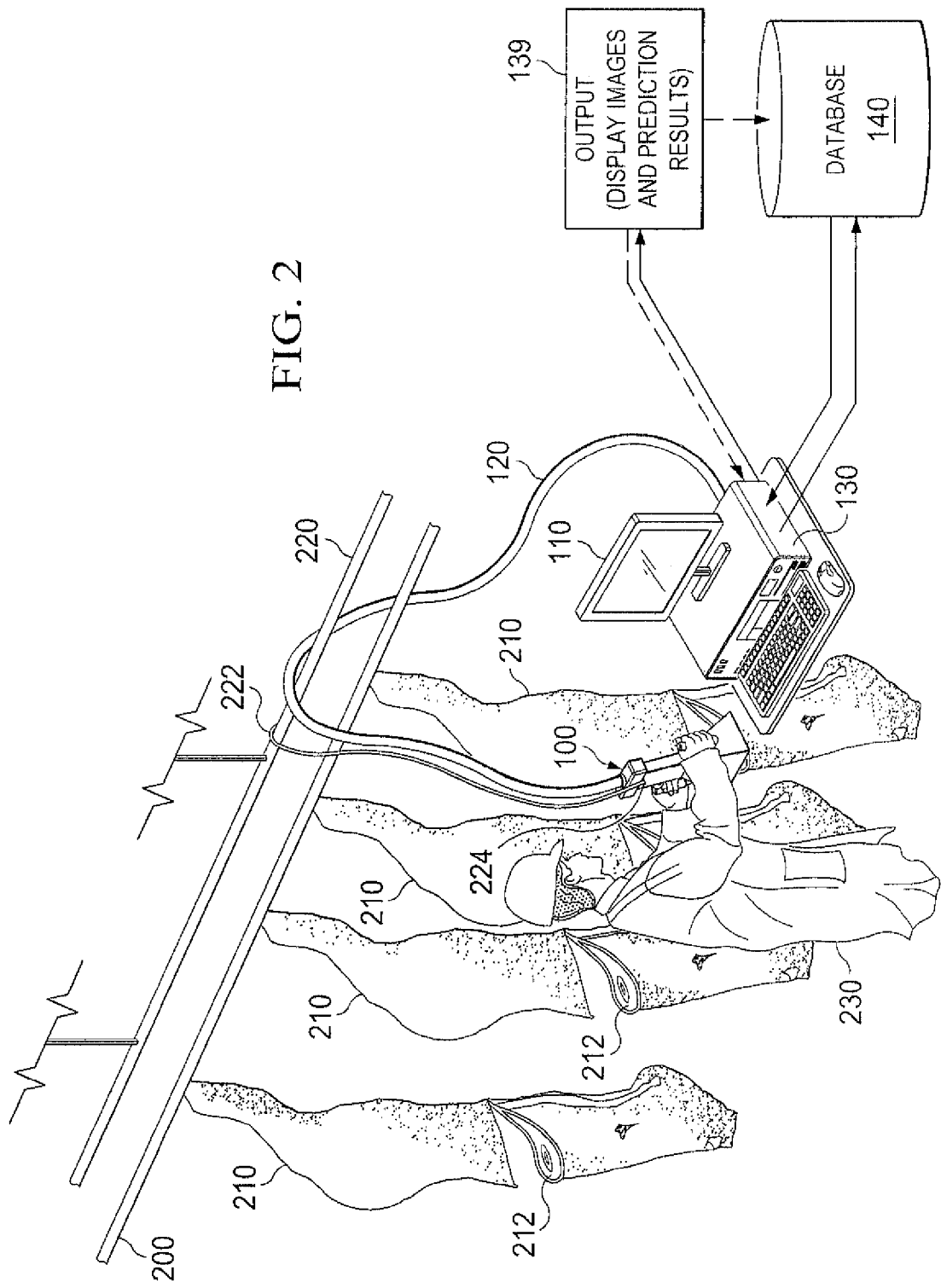
FIG. 2 depicts the components of a multispectral imaging system.

Now referring to FIG. 1 and FIG. 2 which illustrate the use of the system and method in a conventional meat processing plant, an operator is shown placing the camera on a ribeye steak portion of a beef side. This portion is routinely used for grading evaluations in an on-line industrial setting. Alternatively, the camera can be mounted to a holder and the camera operated remotely or automatically in an industrial meat processing facility.

The system and method of the invention can provide several characteristics of the meat sample, but is especially advantageous for prediction of meat tenderness since it is a reliable nondestructive technique that can be employed for rapid and accurate prediction of meat tenderness, particularly in the meat processing (on-line) setting.

Meat tenderness is complex and is directly influenced by a wide variety of biochemical traits, which can broadly be described as myofibrillar in nature (associated with the properties of the myofibril—the structural and contractile component of the muscle), connective tissue in nature (associated primarily with collagen content and properties), and lipid in nature (predominately associated with intramuscular fat content). Biochemical properties include, among others, muscle pH (an indication of muscle acidity), sarcomere length (an indication of the degree of muscular contraction), water holding capacity (a measure of the ability of meat to retain its inherent moisture content), a measure of muscle proteolysis (e.g., degradation of troponin-T, a muscle-specific protein—an indication of the fragility of the muscle fiber), composition (fat, moisture, protein and ash content), and content of soluble, insoluble, and total collagen. A combination of these, and other, characteristics influence meat tenderness, as destructively measured mechanically (e.g., using a Warner-Bratzler shear apparatus or slice shear force) or by trained taste panelists.

The multispectral imaging system and method disclosed herein represents an improvement over hyperspectral imaging to predict meat tenderness, particularly with respect to on-line implementation since it provides increased rapidity of image acquisition and analysis and sufficient data which can be transformed by the system to a forecast of meat tenderness at a time ($t_1$) as well as properties of the meat at time ($t_0$). The output of the system and method can be made known rapidly at the site of analysis. Hyperspectral imaging to determine material properties of meats and other tissues was disclosed in U.S. Patent Application Publication 20080199080, filed Feb. 21, 2008 as Serial Number 035080 and is herein incorporated by reference as if set forth in its entirety. Hyperspectral imaging collects images generally in excess of about twenty five wavelength bands and most often hundreds of wavelength bands in a contiguous manner. In a hyperspectral image, each wavelength band usually overlaps with another wavelength band to the right and the left of it on the spectrum. Because of the overlap, the hyperspectral image acquires data from all wavelengths, even if the wavelengths are 5 nm apart. This means the wavelengths are "contiguous." For example, a hyperspectral image may consist of 101 wavelength bands covering 400-900 nm at 5 nm intervals. It generally requires about 5-10 seconds just to acquire a hyperspectral image. A hyperspectral image contains a large amount of data which tends to be redundant. U.S. Patent Application Publication 20080199080 describes the acquisition of hyperspectral images as well as a dimensionality reduction technique to reduce redundant information. To obtain information of a meat sample, the image processing and analysis time of the hyperspectral image data might take up to 10 minutes. While the information outputted is useful, the time required may be approximately 150 times longer than desired in an industrial setting and the time and processing may add more expense than is desired.

Collecting images at hundreds of wavelength bands and processing the information as may be required with hyperspectral imaging might be a limiting factor in implementing the method in an industrial setting. The multispectral imaging system herein described is cost effective and significantly reduces the image acquisition and processing times in comparison to hyperspectral imaging, because multispectral imaging acquires only the key wavelength bands (less than 25 wavelength bands) as opposed to collecting hundreds of wavelength bands in the case of hyperspectral imaging. As the multispectral key wavelength bands contain less redundant information, there is no need of a dimensionality reduction step when analyzing the multispectral image data and therefore multispectral image analysis is quicker than hyperspectral image analysis. Multispectral imaging can be efficiently implemented on-line in industrial meat processing facilities. In the preferred embodiment, the multispectral image acquisition system for beef tenderness evaluation is fast enough to keep up with a speed at which a beef carcass moves in a production line and so the ability to be implemented in on-line meat processing. Also, the costs are lower and the calibration and optimization of multispectral imaging systems are easier than those of hyperspectral imaging because of the fewer number of wavelength bands.

Multispectral imaging involves capturing images only at a few key wavelength bands. An "image" consists of one or more wavelength bands. A grayscale image consists of 1 wavelength band, a multispectral image has less than or equal to 25 wavelength bands (not necessarily contiguous/sequential wavelength bands) and a hyperspectral image has greater than 25 wavelength bands, often greater than 100 wavelength bands (usually contiguous along the wavelength spectrum).

Figure 3:
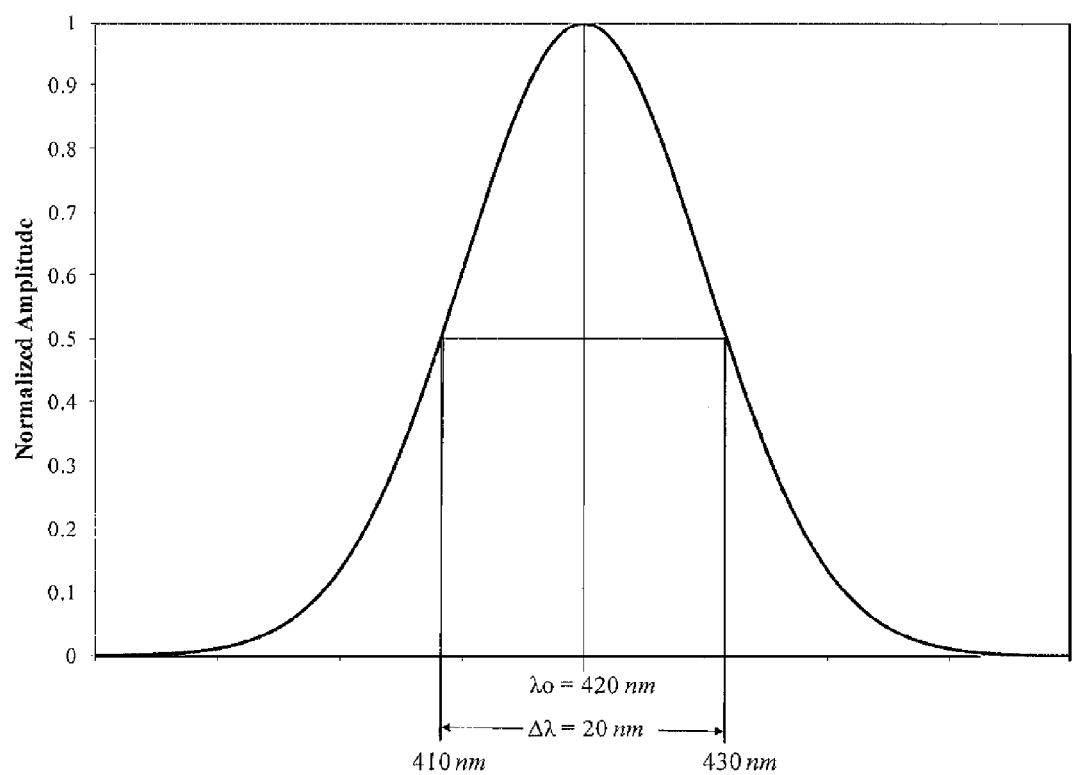
FIG. 3 depicts a representation of a wavelength band, such as employed in the multispectral imaging acquisition system.

A "wavelength band" includes a range of wavelengths. Thus a wavelength band is centered at a specific wavelength ($\lambda_0$) and has a certain bandwidth ($\Delta\lambda$). FIG. 3 illustrates a wavelength band centered at an exemplary wavelength and a bandwidth. For example, if $\lambda_0$=420 nm, and the bandwidth is $\Delta\lambda$=20 nm, full weightage (P=1) would be at 420 nm and half weightage (P=0.5) at 410 nm and 430 nm.

"Wavelength" refers to the location of the band in the electromagnetic light spectrum. For instance, the visible light spectrum is 400-700 nm. The visible/near-infrared (VNIR) spectrum is 400-1000 nm and the near-infrared (NIR) spectrum is 900-2500 nm.

Herein is disclosed a method and system for identifying key wavelengths from hyperspectral images so that these key wavelength bands can be predetermined for use in the multispectral imaging system and method. By acquiring fewer images at key wavelengths that are of interest in predicting meat tenderness and/or other properties, image acquisition and analysis times are considerably reduced, therefore making it feasible for commercial implementation of a multispectral imaging system and method for prediction of meat tenderness and/or other meat properties.

In multispectral imaging of meat, up to about 25 wavelength bands are employed in the image acquisition step. As stated above, the wavelength bands are predetermined so that relevant information about the substance being analyzed is obtained. The predetermined wavelength bands do not need to be regularly spaced or contiguous; rather, they are selected according to correlation with meat properties of interest. Although up to about 25 wavelength bands can be utilized, it is preferred that as few wavelength bands as needed to provide the desired forecast be used. Therefore, though the range of wavelength bands is from about 1 up to about 25, more preferably the range used is from 2 to 12 or from 4 to 8. Alternatively, the key wavelength bands can be employed by their predetermined association with particular characteristics. For example, at least one key wavelength bands correlated with fat characteristics and at least one key wavelength bands correlated with protein characteristics of the meat could be employed. As yet another option, wavelength bands associated with other biological characteristics of interest may be utilized. The system and method for determining the value of the predetermined wavelength bands is disclosed herein, infra.

Characteristics of Meat Obtainable with Multispectral Imaging System and Method

The multispectral imaging system can be adapted for the analysis of any type of meat or tissue for which characteristics can be correlated with information from the imaging. One of the characteristics which is of tremendous importance to the meat industry is tenderness; however other characteristics (some of which are related to tenderness and some of which are not) may also be forecasted with the multispectral system and method of the invention. Such characteristics include, inter alia, flavor, aroma, juiciness, water holding capacity, moisture content, ash content, fat content, protein content, pH, sarcomere length, collagen content, and degree of proteolysis (for example troponin T degradation or degradation of other proteins) and combinations thereof.

The multispectral imaging system is effective for improving the processing of beef because it can forecast characteristics of the meat at a later time ($t_1$) and it can also rapidly provide quality grading and yield grade factors. In addition, it can increase the speed of obtaining grading and yield information as compared to conventional methods, On-Line Use of Multispectral Imaging System and Method in a Meat Processing Plant (On-Line Implementation)

Referring to FIG. 2, in an industrial production location, beef carcasses are split into sides (210), and the sides hung onto a chain (200) which can move the sides into a refrigerated area and through the meat processing steps, or line. The process is referenced as "on-line" processing. The chain (200) moves at a rate of five to nine (5-9) seconds/side. In a conventional processing system, a worker (not shown) will rib each side so that when the sides reach a location where conventional grading occurs (pursuant to United States Department of Agriculture protocols), the sides are presented in a ribbed condition. When the side is ribbed, a ribeye steak (212) is exposed and this is preferably utilized for imaging. FIG. 1 and FIG. 2 illustrate a number of beef sides on a line moving past an operator. In the system and method for multispectral imaging, it is most preferred to select a location for image acquisition along the production process, at which location a side will arrive in a ribbed condition.

As the sides move on the chain (200), they are not perfectly stationary at any point in time. Ideally, the side (210) and camera (100) are both stationary. An operator (230) places the camera (100) over the exposed ribeye (212) and acquires the image while holding the camera (100) still (with no relative motion) in relation to the ribeye (212). Practically, however, when the system and method is employed in a conventional meat processing plant, the line of sides would remain moving on the chain (200). In such case, measures are taken to ensure that when each image is acquired, relative motion of the camera with respect to the ribeye is eliminated. In order to acquire the multispectral image, a camera can be secured temporarily to the meat, while the image is acquired, via a mechanical gripping means, or alternatively the side can be stopped with a mechanical gripping means for a brief but sufficient time to allow the image to be acquired with the ribeye remaining stationary relative to the camera.

The camera can be temporarily secured to the ribeye with a mechanical grip means which holds the camera (which is also preferably secured to a camera support means (222)—here shown as a cable attached to the camera (100) at attachment (224) and is also attached to overhead support structure (220). It is preferred that camera support means have retractable functionality so that the camera can be pulled down by the operator when needed and retracted upwardly when not needed. Other types of camera supports can also be used. Having a support for the camera to bear the weight of the camera in the vicinity of the image acquisition area will keep the camera nearby when not in use and will assist the operator in bearing the weight of the camera when it is in use. In one embodiment, an operator can place and secure the camera (100) to the ribeye with a mechanical grip means, then actuate the camera trigger. Once all the bands are acquired, the mechanical grip means is preferably released automatically. The camera support means can then return the camera back to the operator, or the operator can grab the camera from its position a bit further up the line, and the operator can then secure the camera to the ribeye of the next side to be analyzed.

Alternatively, the advance of the side on the chain (200) can be stopped with a mechanical gripping means which will hold the side stationary relative to the camera while the image is secured. In an automated process, the line can be engineered with techniques known to the art to provide for a stoppage of line to enable the image to be taken.

In still another variation, a camera which can take the multispectral image while the carcass is in motion can be used if available.

Before using multispectral imaging to obtain data from meat in an industrial setting, a number of key wavelength bands would have been predetermined. A system and method for predetermining these key wavelength bands are disclosed herein infra. Images of the meat are acquired at these predetermined key wavelength bands. In a preferred embodiment, an image acquisition system obtains images only at preselected key wavelength bands for a particular meat sample.

In an alternative embodiment, a multispectral image acquisition system comprises a kit which can be provided to a customer, such as a meat processing plant. The kit comprises information as to which key wavelength bands the customer should use in a method of meat analysis or tenderness forecasting. The kit may be customized for the customer so that a forecast or determination of specific parameters of interest is provided. The kit may further comprise an image acquisition system and an image analysis system. The kit may further comprise a display module that outputs the determined properties of meat. Alternately, images acquired may be collected and electronically stored. The electronically stored images can be analyzed in an image analysis system located remotely from the image acquisition system.

Images are acquired using an image acquisition system which is preferably adapted for acquisition of multispectral images only for key wavelength bands that are of interest. The image acquisition system comprises a camera, a wavelength dispersion unit, a lens, a housing and lights to illuminate the object for the image acquisition. Components of a preferable image acquisition system are commercially available, but a most preferred image acquisition system is specially adapted to acquire multispectral images from meat.

Figure 4:
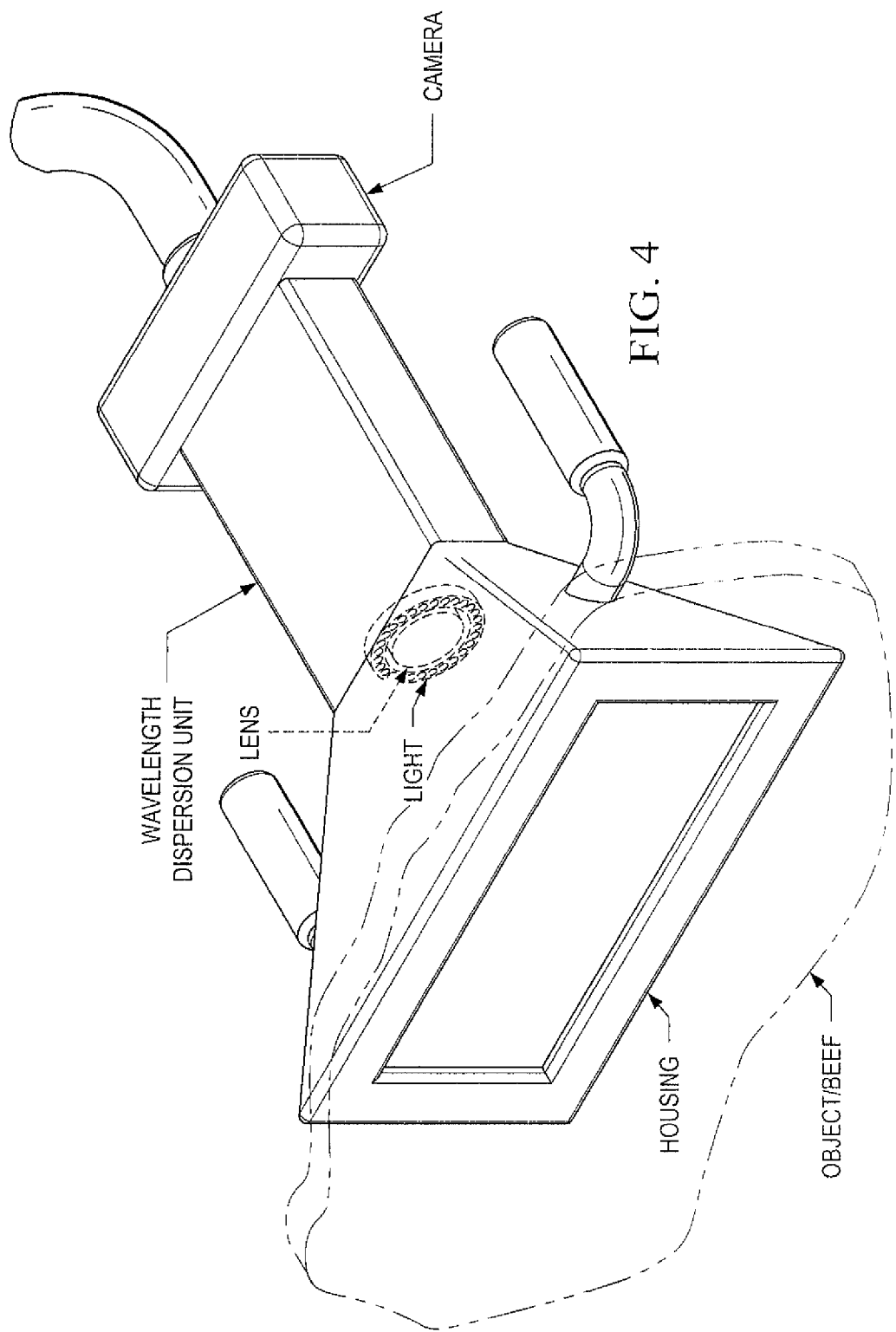
FIG. 4 depicts an exemplary image schematic image acquisition camera and component parts thereof.

FIG. 4 illustrates an exemplary schematic image acquisition system. The exemplary image acquisition system comprises a housing, a camera, a wavelength dispersion unit for selection of the key wavelength bands, an illumination means (lights), and a handle for holding the device by a user.

The position of the camera and type (focal length) of lens determine the distance of the camera from the object to be properly focused and to obtain an image with a desired field-of-view (FOV). The housing of the image acquisition camera may be adapted to provide a preselected distance between the camera and the object and an area for image acquisition of a predetermined size. For example, for an imaging area of 5 inch by 7 inch, a distance of about 21.8 inches was found to be appropriate for a 25 mm focal length lens (Hyperspectral CoastalOpt lens, JENOPTIK Optical Systems, Jupiter, Fla.). The housing and lens should not attenuate the reflected light spectrally from the ribeye or object. The housing should further comprise calibration targets, so that calibration targets and meat are imaged simultaneously on the same FOV in each and every multispectral image.

The camera component has a lens through which reflected signals from an object pass to a two-dimensional array of sensors (also known as 'focal plane array (FPA)') located internally in the camera. A sensor is a detector that can quantify the amount of light photons. Based on the type of sensor, it can quantify light in various electromagnetic regions. For example, a charged-couple device (CCD) sensor is sensitive in the region of 400-1000 nm. An Indium-Gallium-Arsenide (InGaAs) sensor is sensitive either in the region of 900-1700 nm or 1700-2500 nm, depending on how the sensor was treated and coated. An exemplary InGaAs camera appropriate for use in the system and method of the invention is Model: XEVA-USB-LIN-k1.7-256-TE1 (XenlCs, Belgium). A preferred camera comprises a sensor that should be able to sense signals from all key wavelength bands. If key wavelengths cover both VNIR and NIR regions, then two cameras are required. An optical mirror could be used to split the reflected signal and two cameras could image the object (steak) simultaneously in two regions namely VN IR and NIR.

The lens of the image acquisition system is preferably a chromatically corrected lens. Typically, the focus of a standard camera lens changes with the wavelength of the band pass filter employed. Consequently, one wavelength band may be well focused, while another wavelength band might be out-of-focus, causing information on image texture to be compromised or lost. Chromatically corrected lenses are specially designed lenses which correct the focus for an entire wavelength band region and therefore should preferably be used in the system of the invention. An exemplary chromatically corrected lens in the wavelength range of 400-1700 nm appropriate for use in the system and method of the invention is Hyperspectral CoastalOpt lens (JENOPTIK Optical Systems, Jupiter, Fla.).

The image acquisition system further comprises an illumination means which shines light onto the object (meat) to be imaged. Imaging can be done either in reflection mode or transmission mode. In the system and method of disclosed herein, the reflectance mode is preferably utilized, meaning the reflected light shone upon the object by the illumination means is imaged. In some other applications, for example for characterizing other type of tissues, transmittance mode of images can be used. The image acquisition and analysis components and methods can be adapted accordingly.

The illumination required is equivalent to approximately two EZK 12 volt, 150 watt bulbs. A DC power source or converter can be used to convert 110 V AC to 12 V DC. In a preferred embodiment, a DC power source is used, because the light output from a DC power source is more stable than an AC power source. The illumination means must provide light in the key wavelength bands identified for a particular application. In one embodiment, a broadband light source such as a tungsten-halogen lamp can serve as the illumination means. It is preferred to have equal light output intensity for all key wavelengths. If needed more than one type of light source can be used.

The illumination means can be secured to said camera. Preferably, this can be employed as a ring light surrounding the lens of the camera where it will illuminate the object analyzed.

In an alternative embodiment, the illumination means is not secured to the camera or a supplemental illumination means is employed. The illumination means can comprise a diffuse lighting system which causes uniform diffuse light to be applied over the object. For example, lights can be provided at the sides of the object, typically on the same surface level as the surface of the ribeye. A hemispherical dome is set up over the object. Preferably, the dome is painted with 99% reflective optical standard white paint. The light from the bulbs will reflect up to the white dome which will in turn cause uniform diffuse light to be applied over the object.

In another embodiment, the lighting can be supplied by light emitting diodes (LED). The spectral output of said LED lights must be selected to match the predetermined wavelength bands. A lighting hood (the housing for the lighting) can be painted with white reflective paint. The lighting hood also serves as means to maintain a certain distance of the object from the lens. Also, it houses (protects) lighting, the lens, and maybe even the camera. The lighting hood may also contain a white plate, a gray plate, and a black plate on the edges of the field-of-view. This will provide acquisition of the image and calibration targets in each and every image, thus permitting accurate calibration of the multispectral image.

The image acquisition system further comprises a wavelength dispersion unit which splits the light into several light components based on its wavelength. The wavelength dispersion unit can be selected from a spectrograph, a set of bandpass filters, an (liquid crystal tunable filter) LCTF system, an (acousto-optic tunable filter) AOTF system or any other system which provides the desired function.

A spectrograph is a sophisticated version of a prism. A prism can split a white light into a rainbow of colors. Similarly, a spectrograph can split the light into various wavelength bands in a contiguous manner. Thus, it is commonly used in hyperspectral imaging. In the case of multispectral imaging, a spectrograph can be used if the camera can be programmed to partially transfer the frames—meaning that only a few specific wavelength bands are transferred to the computer in the image analysis component of the system. In this case, the camera will still acquire the complete wavelength range similar to hyperspectral imaging. However, the camera transfers only part of the frame (only a few key wavelength bands) to the computer. Image acquisition time is partially reduced because it is not transferring all the bands. Image analysis time is considerably reduced, as only a few key wavelength bands are analyzed.

Preferably, a "band pass filter" is employed as the wavelength dispersion unit used in conjunction with the camera to filter out only a specific wavelength band and reject other wavelength bands. By putting a band pass filter in front of a camera lens, one collects image only at that wavelength band. By having a series of band pass filters which can be rapidly changed, one can acquire images at a series of wavelength bands which together will constitute a multispectral image. Filters can be placed in a wheel and rotated mechanically rapidly in succession in front of the camera lens after each wavelength band is acquired.

More preferably, the wavelength dispersion system comprises a liquid crystal tunable filter (LCTF). An LCTF employs electrically controlled liquid crystal elements to select a specific wavelength of light for transmission through the filter at the exclusion of all others.

Most preferably, the wavelength dispersion system is an AOTF system. AOTF systems consist of a crystal in which radio frequency (RF) acoustic waves are used to separate a wavelength band of light from a broadband light. The wavelength of light selected is a function of the frequency of the RF applied to the crystal. Thus, by varying the frequency, the wavelength of the filtered light can be varied.

When the number of key wavelength bands is from two to four, the multispectral imaging system can be implemented by using a beam-splitter with multiple imagers or cameras. Reflected light from the object may be split into two light paths using a beam splitter mirror and the two light paths then passed through two different band-pass filters and two cameras, resulting in the acquisition of two images at two different wavelength bands. The split light can be further split.

In a preferred embodiment, the image acquisition system comprises an acousto-optic tunable filter (AOTF) imaging module, a radio frequency (RF) unit, a CCD camera having a chromatically corrected lens, and an illumination system secured to the camera in a ring surrounding said lens.

The AOTF optical head preferably provides a spectral sensitivity in the visible-near infrared region (VNIR) ranging from 400 nm-1000 nm and has a spectral resolution of at least 3.8 nm.

The RF unit provides an electronic signal to the AOTF transducer creating a grating pattern that controls which wavelengths of light are allowed to pass by the filter. Preselected wavelength bands can be programmed in the RF unit so that it sends the signal to the AOTF unit to acquire only those preselected bands.

The image acquisition system incorporates means which provide a working distance. Preferably housing of the image acquisition system is dimensioned so that the camera is at a predetermined distance from the object. This permits definition of the field-of-view (FOV) captured in the image. It is preferable to dimension the system so that the entire FOV of the desired object (e.g. a ribeye steak, 6×8 inches) can be imaged in proper focus. Providing a customized image acquisition system having housing of a fixed dimension and structure adapted in this way allows all these settings to be uniform from sample to sample. The image analysis system of the multispectral imaging system and method of the invention can utilize the same image processing algorithm to analyze images.

The FOV is preferably at least 5 inch×7 inch and more preferably 6 inches by 8 inches which is the general size of a whole ribeye. Most preferably, FOV reflects the size of essentially the entire sample. For some forecasts or analysis, the area of the sample enters into the computations. This is the case, for example, with grading of beef in which ribeye area is a factor.

Preferably, the image acquisition system further comprises or can be connected to a monitoring means. The monitoring means can be a display monitor, such as a computer monitor or a television screen, in communicative relationship with the camera in order to display the images captured and to detect any faults in the process. For instance, if an operator shakes the camera and/or failed to place the camera on the specimen correctly, a program in the camera can identify those faults and alert the operator by displaying a warning on the monitoring means. The monitoring means can also serve a purely visual function to assist the operator in proper placement of camera so that the complete FOV can be acquired. In another embodiment, the monitoring means may also be connected to the image analysis system discussed below.

Conventionally in beef processing plants, the carcass sides are cut (ribbed) between the 12th and 13th rib to expose a cross section of the ribeye muscle. A cut carcass side is shown in FIG. 1 and FIG. 2. This cut surface represents the surface of a beef rib steak.

Using the multispectral imaging system and method, images of the longissimus dorsi cut between the 12th and 13th rib of a hanging carcass side are obtained with the image acquisition system. The image acquisition system may be mounted on a mobile cart or the like which preferably has means for height adjustment. Alternatively, the image acquisition system may be installed on an overhead structure which will allow for the intended use and placement. In FIG. 2, an operator is utilizing the image acquisition system with an overhead support.

Taking the images involves placing the image acquisition system on the sample, actuating the image acquisition system using a trigger and holding it steady for approximately two (2) seconds or less. The trigger will switch on the light and send a signal to the camera to acquire the data. In a preferred embodiment, this trigger also actuates a mechanical gripper system that will hold the image acquisition system with the carcass.

Use of Multispectral Imaging to Obtain Objective Quality Grade, Marbling Score and/or Yield Grade Once the rib area is cut as described above, the multispectral image can be taken immediately. (In contrast, standard grading and marbling scores provided by human graders require waiting approximately 15 minutes to allow the cut muscle to oxygenate, during which time the color of the muscle changes from a purplish-red to bright red. This allows time for the marbling (intramuscular fat) to become visible to the human eye).

Thus, the multispectral system and method disclosed herein eliminates the lag or delay in processing and provides more information than can be provided by observation with the human eye. Currently, it is standard in the United States and some other countries to provide a marbling score and quality grade from observation with the human eye. A multispectral image taken immediately after the 12th/13th rib interface is exposed can provide these same marbling and grading factors objectively. Cost and efficiency advantages may be realized with this more rapid and objective determination of beef quality grades.

In addition, conventionally at the time of quality grading, U.S. Department of Agriculture yield grade factors are also assessed and a yield grade is assigned. With use of the system and method of the invention, information obtained from the multispectral image (ribeye muscle area, fat thickness), coupled with data easily obtained from the carcass (hot carcass weight and percentage of carcass weight as kidney, pelvic, and heart fat) can be used to establish the appropriate yield grade without the necessity of the lag time.

The system and method of the invention further comprises an image analysis or processing system, preferably in communicative relationship with said image acquisition system and display means. After the multispectral image is taken, the data are transmitted to the image analysis or processing system which analyzes it for the parameters of interest and outputs the determined characteristics of the meat.

The image analysis system comprises a computer having a computer processor containing algorithms and methods to analyze the acquired image to perform calibration, region-of-interest (ROI) selection, textural feature extraction, and tenderness prediction. In one embodiment, the computer is external to the camera and the camera communicates the image data to said computer which saves it on its hard drive. The image processing program reads the image from the computer hard drive and executes the steps depicted in FIG. 5. In another embodiment, the camera holds image data in "random access memory" (RAM), which is a virtual memory space in an on-board processer. Image processing operations are then done in RAM and only results will be stored in the hard-drive. Before the next image is acquired, the RAM is cleared and will be ready for the next image.

Figure 5:
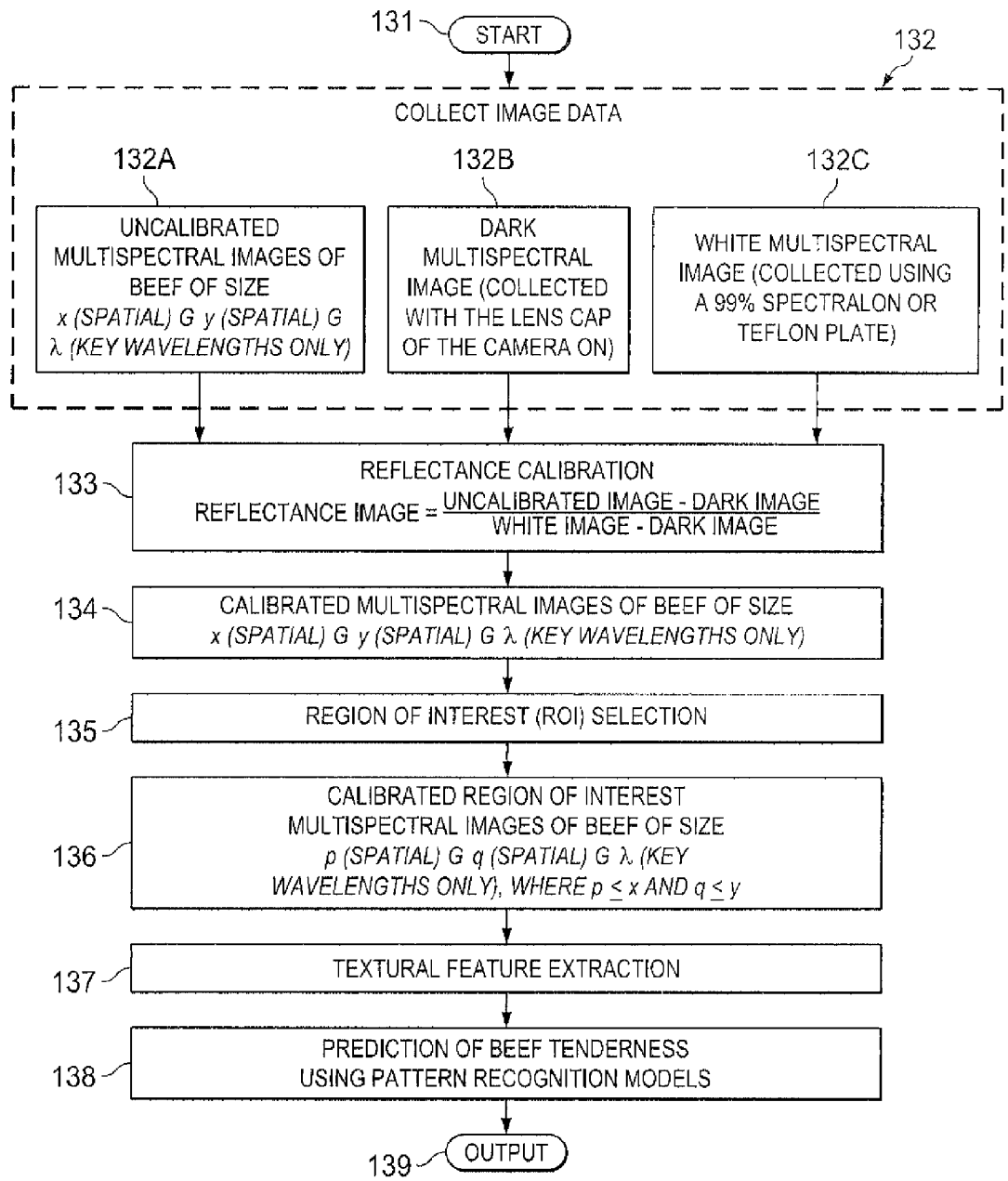
FIG. 5 is a flowchart depicting the image analysis system computation steps.

FIG. 5 is a flowchart depicting the steps of image processing which are accomplished by the system. The multispectral imaging system and method system starts at (131) and involves image acquisition (132) as discussed above. In addition to the sample images (132 A), dark images (B) (could be dark calibration target in the FOV) and white images (C) (could be the white calibration target in the FOV) are collected for calibration purposes. Step 132 occurs in the camera component of the system. The image data are then transmitted to the computer using one of the means discussed elsewhere herein. The computer processes the received image data (133) to a reflectance image. Next, the reflectance image is processed to a calibrated multispectral image (134). A region of interest (ROI) is selected (135) by criterion programmed into the computer resulting in a calibrated ROI (136). The computer program then extracts textural features from the calibrated ROI (137) and pattern recognition models programmed into the system compute a forecast (tenderness forecast exemplified) (138). The output or results (139) can be obtained from the computer by conventional means of access to the output report generated or may be displayed on a monitoring means.

As stated, it is contemplated that the image analysis system will be in communicative relationship with a monitoring means as discussed above and may house software which will receive input about the image acquisition process and alert the operator in case of fault.

The image analysis system further preferably comprises a communication cable or a communication/power cable. As best seen in FIG. 2, exemplary communication/power cable (120) provides power to the camera, wavelength dispersion unit, and lighting system. It also can communicate commands from the computer (130) to the wavelength dispersion unit as to which wavelength bands to use for imaging the sample. The collected image data are then transferred to the computer through the communication cable (120). The cable can be anchored on a structure (220) above the analysis station to support its weight during operation. The image acquisition system components may have a separate support cable (222).

The communications cable which may be connected to the camera (100) and the computer (130) may enable transfer of image data in real time. Alternatively, the image data can be transferred to the computer upon user actuation of the necessary commands. The images can also be transferred to the computer through other means known to the art such as wireless transmission or Bluetooth™ transmission.

In the preferred embodiment, calibration targets (white and dark) are imaged in the field-of-view. Thus, each and every multispectral image of ribbed surface of the carcass will also contain the images of calibration targets.

From the image, the regions of calibration targets are separated by a simple thresholding operation. Because the region of the white plate is the brightest spot in the image, it can be easily separated. Similarly, the region of the dark plate has the lowest pixel values (gray-level values) in the image, so it can also be easily separated. The mean values of white and dark regions are determined at each wavelength band. Corresponding bands in the multispectral image are calibrated by the white and dark values, as shown in Equation 1. By calculating reflectance, differences due to illumination from one sample to another sample are minimized or eliminated $$ReflectanceImage = \frac{RawImage - Dark\ Value}{White\ Value - Dark\ Value} \quad \text{Equation 1}$$

Textural features have to be extracted from the ribeye area. The ribeye area is irregular and close to oval in shape. However, some of the image textural analysis algorithms require the image to be square or rectangular. Therefore, a Region-of-Interest (ROI) around the center of the image is selected. The ROI size is selected in such a way that the ROI fits within the ribeye area. It should be noted that, if the image is acquired such that the entire field-of-view occupies the ribeye area, then this step is not necessary. In other words, the entire FOV is the ROI.

Textural features can be directly extracted from these bands and statistical models such as discriminant analysis can classify the carcass based on tenderness or other selected properties.

Textural features can be extracted from each band in a multispectral image using the spatial gray-level co-occurrence matrices (GLCM) method. The GLCM algorithm creates a co-occurrence image based on the relative frequencies (gray-level values of the co-occurrence image) with which a pixel of gray level 'i' occurs with a neighboring pixel of gray level 'j' separated by a relative distance 'd' and a given angle 'θ'. The notations 'i' and 'j' denote the gray level values of the original image and they range from 0 to $2^n-1$ ('n' can be any positive integer; the higher the value of 'n', the longer the GLCM algorithm takes to compute the textural features; We used an 'n' value of 8 which we herein disclose to be optimum although other values can be used; the size of the co-occurrence image will be $2^n-1 \times 2^n-1$). We used a d value of 1 and four θ values: 0°, 45°, 90° and 135° (degrees). The textural features computed from four angles are then averaged to get rotationally invariant textural features.

The following eight textural features are computed from the co-occurrence matrix or image.

Mean: The average gray-level value of the co-occurrence image.

Variance: A measure of how the gray-level values of the co-occurrence image are dispersed with respect to the mean gray-level value of the co-occurrence image.

Correlation: A measure of linear dependencies of gray-level values of the co-occurrence image.

Contrast: Measures local variation in the co-occurrence image.

Dissimilarity: Measures the dissimilarity between two neighboring pixels offset by a given distance and angle in the co-occurrence image.

Second Moment or Energy: A measure of textural uniformity, i.e., the repetition of pixel pairs.

Homogeneity: Homogeneity is also known as an inverse difference moment, which is inversely proportional to the contrast of an image.

Entropy: An indication of the complexity or information content within an image—i.e., the more complex or detailed an image, the higher the entropy value.

Statistically, it is often important to evaluate the distribution of data points. This can be done by assessing skewness and kurtosis. Skewness is a fourth order statistics that measures asymmetry of the data with respect to the mean of the data. A normally distributed data has a skewness value of 0. A negative skewness value indicates a left-skewed distribution, where as a positive skewness value indicates a right-skewed distribution. Kurtosis is also a fourth order statistics that indicates how outlier-prone a distribution is. The normal distribution has a kurtosis value of 3. If the kurtosis value of a given data is greater than 3, then the data are more outlier-prone than that of the normally distributed.

Textural features can also be extracted using other textural analysis algorithms. GLCM extracts textural features in the spatial domain. Fourier transform converts the image to the frequency domain and features can be extracted in the frequency domain. Higher frequency indicates finer textures, while lower frequency indicates coarser textures. Wavelets and Gabor filters can provide joint spatial-frequency domain textural features. Another method is development of a covariogram.

A pattern recognition algorithm can then be used to predict meat properties from extracted textural features. Discriminant analysis such as canonical discriminant model, Fisher linear discriminant model, logistic regression, or clustering approaches can be used to classify carcasses into different categories. Regression approaches such as linear regression, nonlinear regression, principal component regression, partial least squares regression methods can be used to predict the tenderness scores. Other approached such as fuzzy logic, artificial neural networks, and genetic algorithms can also be implemented.

After the image data are extracted and analyzed in the image analysis component of the system, a forecast or prediction is outputted to a display means, thus culminating in the generation of objective information about the sample. A forecast output is relevant to properties at time ($t_1$), such as tenderness; while properties at the time of assessment ($t_0$) such as quality and yield grades are a prediction output.

The computer may also have a labeling program and communication means enabling it to send information discerned or computed about the carcass to an electronic tag secured to the carcass. Such tags are known in the art and may be employed by a meat producer to store all data relevant to a given carcass thereon. The computer labeling program can send a forecast of tenderness as well as any other data to the carcass tag. This allows the system and method of the invention to output information directly to the item under analysis, thereby fostering better individual carcass management by the processing facility.

Identification of Key Wavelength Bands for Predicting Meat Quality

To develop and implement a multispectral imaging system appropriate for an application of interest, two steps namely (1) identification of key wavelength bands from hyperspectral images and, (2) evaluation of key wavelength bands for predicting meat properties, are needed. It should be noted that once key wavelength bands have been identified for a desired application, they can thereafter be utilized for that application without the need to re-identify said wavelength bands.

After the key wavelength bands are identified, they are used in the multispectral imaging system and method to forecast tenderness and/or other characteristics of meat described above.

Herein are disclosed methodologies to identify a few key wavelength bands that can be used in the multispectral imaging system of the invention. Key wavelength bands for different material properties can be identified separately and integrated into a single multispectral imaging system for the assessment or prediction of several material properties simultaneously.

Figure 6:
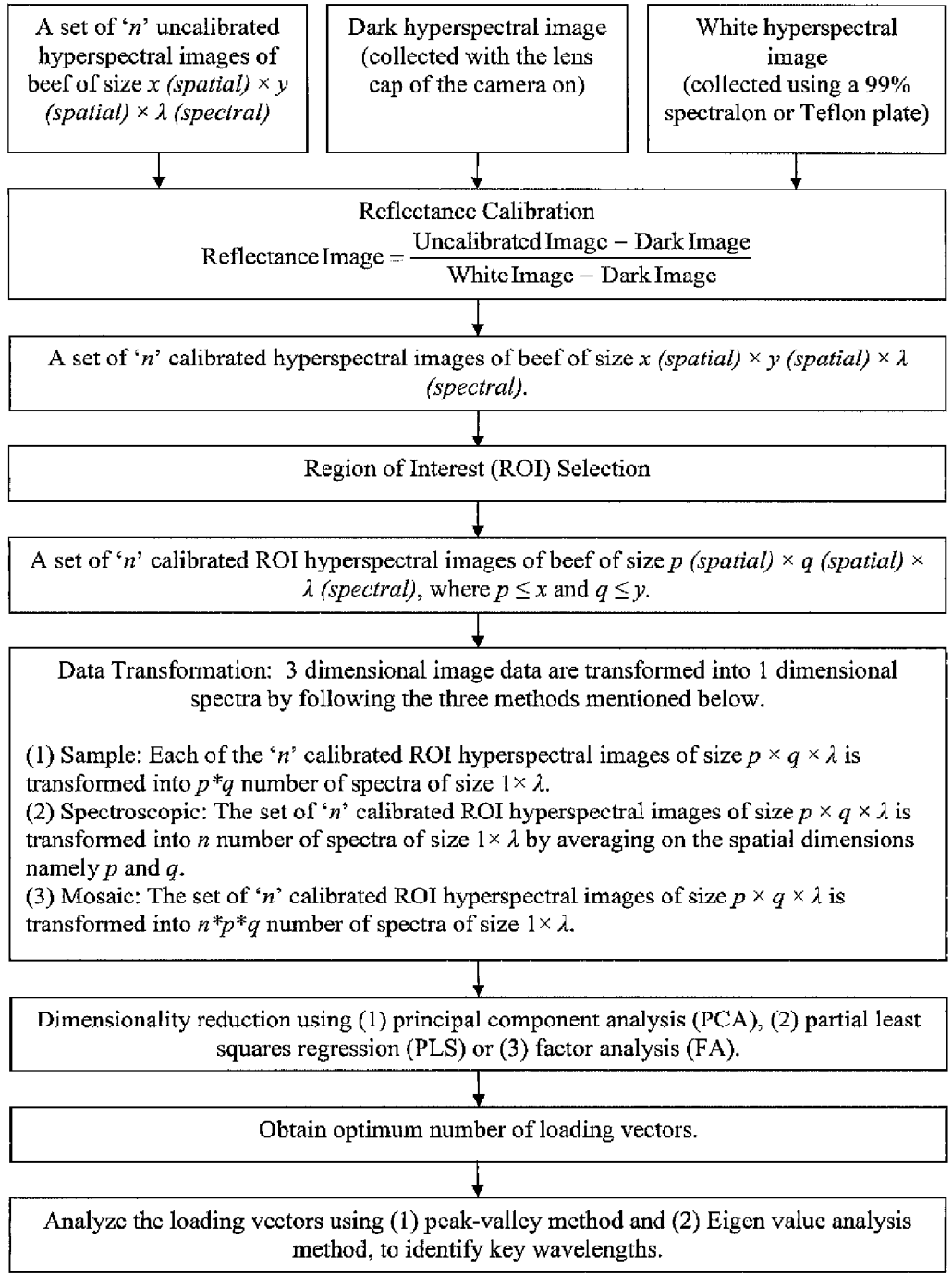
FIG. 6 is a flowchart representing a process for predetermining wavelength bands for use in a multispectral imaging system.

Identification of key wavelength bands procedures include the following steps: (1) calibration of hyperspectral images; (2) selection of region-of-interest (ROI); (3) data transformation; (4) dimensionality reduction; (5) analysis of loading vectors to identify key wavelength bands. Each step is described below. FIG. 6 is a flowchart representing a process for predetermining wavelength bands for use in a multispectral imaging system.

After acquiring hyperspectral images, they are calibrated using a dark and white hyperspectral image. By calculating reflectance, differences due to illumination from one sample to another sample are minimized or eliminated.

After calculating reflectance, a Region-of-Interest (ROI) around the center of the image is selected. For beef, the ROI size is preferably selected in such a way that the ROI fits within the ribeye area for tenderness assessment. It should be noted that if the images are acquired at the center of the image, then the ROI is the entire image or field-of-view.

The three-dimensional hyperspectral image (two (2) dimensions are spatial and the other dimension is spectral) is then transformed into a one (1) dimensional spectra. It can be transformed by using three methods: (a) sample; (b) spectroscopic; and (c) mosaic. Each method is described below.

In 'sample' data transformation, each ROI hyperspectral image of size p (spatial)×q (spatial)×λ (spectral) is transformed to p*q spectra of dimension (1×λ). Further dimensionality reduction is performed within each hyperspectral image separately. Dimensionality reduction results in obtaining loading vectors. The loading vector gives the coefficient or weightage value at each wavelength in determination of new uncorrelated variables. Extreme (high positive or low negative) values indicate that those wavelengths are important in determination of the new uncorrelated variable and therefore meat properties. The loading vectors can vary from hyperspectral image of each sample to other samples. This type of analysis explains within-sample variation and ignores between-sample variations.

In 'spectroscopic' data transformation, a set of 'n' calibrated ROI hyperspectral images of size (p×q×λ) is transformed into n number of spectra of size (1×λ) by averaging on the spatial dimensions namely p and q within each hyperspectral image. The pixels of the ROI for each image are averaged and a one-dimensional spectrum is obtained for every sample. All n spectra were used for further dimensionality reduction step. This type of analysis ignores within-sample variation and focuses on between-sample variation.

In 'mosaic' data transformation, the set of 'n' calibrated ROI hyperspectral images of size p×q×λ is transformed into n*p*q number of spectra of size 1×λ. All n*p*q spectra were used for further dimensionality reduction step. This type of analysis explains both within-sample variation and between-sample variation. Since the number opf spectra (n*p*q) is very large, more computation time, and sophisticated hardware are required as compared to the other two methods. However, this step is an offline computation and needs to be completed only once for a certain population of carcasses. Thus, this method does not need to be computed real-time.

Once a set of spectra are obtained using any one of the data transformation methods explained above, the next step is dimensionality reduction. These spectra are exported to a chemometric modeling software such as Unscrambler® 9.6 (Camo Inc., Woodbridge, N.J.). The spectra are mean centered, fed into the dimensionality reduction algorithms, and loading vectors are obtained. It can be performed using: (a) principal component analysis (PCA); (b) partial least squares (PLS) analysis; (c) factor analysis; (d) minimum noise reduction analysis; or (e) entropy-based methods. The first two methods are explained below.

PCA determines new variables or principal component bands such that they explain maximum variation of independent variables (spectral reflectance) alone, while the dependent variables (such as slice shear force values) are not considered.

Partial least squares regression (PLS) is a dimensionality reduction technique similar to principal component analysis (PCA). In contrast to PCA, PLS defines new bands such that they explain variation of independent and dependent variables as well.

The dimensionality reduction step provides a set of loading vectors that can be used to calculate new bands. The first few new bands explain the maximum amount of variation in the original spectra. For example, the first 3 bands can explain over 95% of variation in all spectra in the hyperspectral image.

Note that, loading vectors can be separately obtained for lean and fat pixels, if desired for a particular application.

Loading vectors are then analyzed either using (a) peak-valley analysis or (b) Eigen-value analysis to identify key wavelength bands.

In peak-valley analysis, the loading vectors are analyzed for identifying the wavelengths at which extreme amplitudes (either high positive value or low negative values, which is seen as peaks and valleys in the curve) are observed.

Key Wavelength Bands for Beef Multispectral Imaging

Using the system and method described above, we have identified twelve key wavelength bands in the visible near-infrared (VNIR: 400-1000 nm) and another twelve key wavelength bands in the near-infrared (NIR: 1000-1700 nm) region for beef which can be utilized as predetermined key wavelength bands in the multispectral imaging system and method for analyzing beef and provide data which are correlated with beef tenderness.

Figure 8:
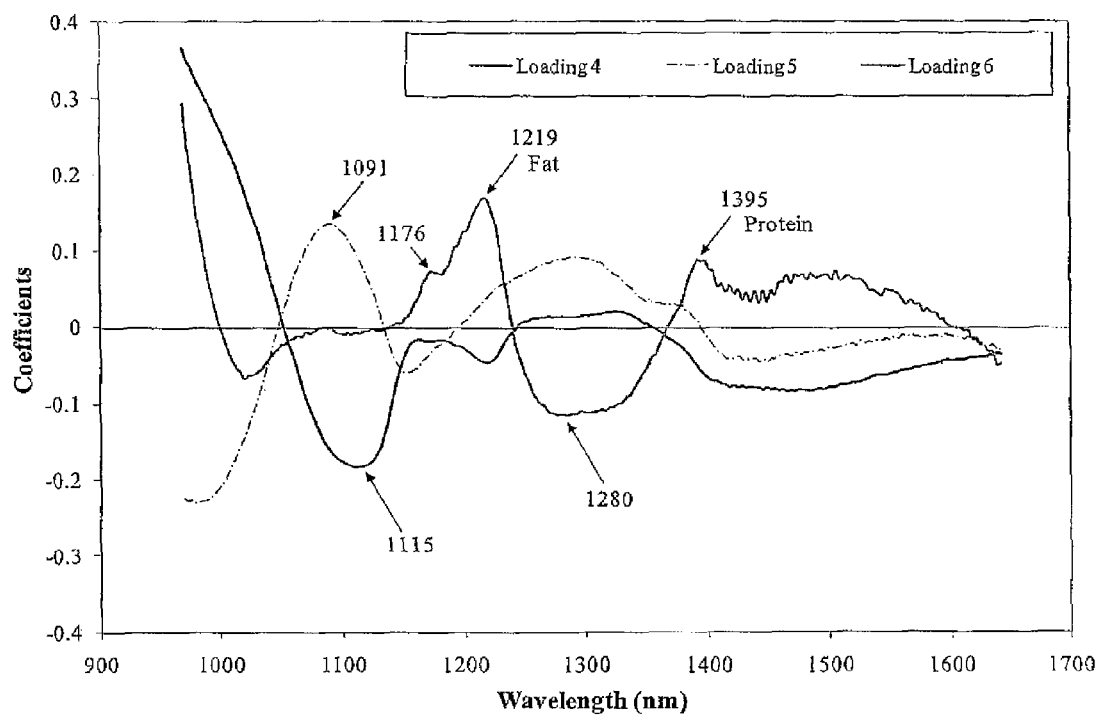
Figure 9:
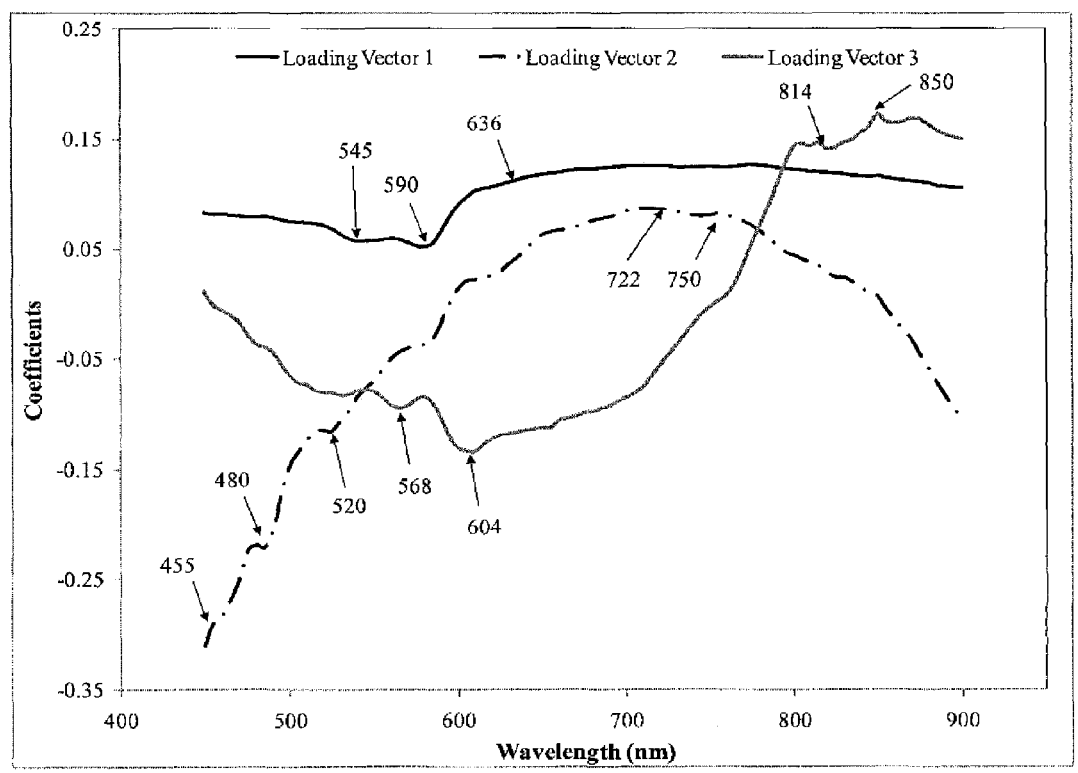
FIG. 9 is a graph plotting wavelengths vs. coefficients and depicting loading (Eigen) vectors of Visible/near-infrared range for multispectral imaging.

In one set of analysis of hyperspectral images acquired in the NIR region, the PLS procedure was used a dimensionality reduction technique and the first 6 loading vectors explained most variation. The peaks and valleys of the loading vectors were significantly different from zero such that they played major roles in constructing the PLS bands. Hence, the wavelengths corresponding to the peaks and valleys of the loading vectors can be considered as key wavelengths. The twelve key wavelength determined for beef in the NIR region are 1057, 1074, 1091, 1115, 1142, 1176, 1219, 1280, 1365, 1395, 1408, and 1462 nm. (FIGS. 7 & 8) In another set of analysis of hyperspectral images in the VNIR region, the following twelve key wavelengths were identified: 455, 480, 520, 545, 568, 590, 604, 636, 722, 750, 814, and 850 nm (FIG. 9).

In case of the predetermined wavelengths for beef multispectral images, it is contemplated that the key wavelengths might vary by ±20 nm. As can be seen from the numbers, the wavelength bands will not necessarily be contiguous.

Although the bandwidth (also known as full width at half maximum (FWHM)) will generally be the same for each wavelength, the fact that there are only a few wavelength for which an image is taken of the sample, it is possible to vary the bandwidth of individual wavelength bands if desired.

For instance, example, if protein absorption has been determined to be at "x" nm, and the absorption range is "x±20 nm, the bandwidth can be set to capture the entire absorption range. For another property, the bandwidth that will capture all relevant information may be y±10 nm. Therefore, in the system and method of the invention, bandwidth can be optimized for one or more of the key wavelengths determined.

Other meats may have different wavelength bands of importance. The disclosed methodology provides a way to determine the wavelength bands for data collection that are correlatable with the tenderness and other properties of the meat.

EXAMPLE 1

Multispectral Analysis of Beef

Twelve key wavelength bands in the NIR—1057, 1074, 1091, 1115, 1142, 1176, 1219, 1280, 1365, 1395, 1408, and 1462 nm were predetermined as related to tenderness classification. For each wavelength band, 8 image-textural features (mean, variance, homogeneity, contrast, dissimilarity, entropy, second moment, and correlation) were extracted using a co-occurrence matrix analysis, thus creating a total of 96 image-textural features per steak image. Using these 96 image-textural features, a canonical discriminant analysis was performed to create two new, uncorrelated variables (canonical variable 1 and 2: Can1 and Can2). These canonical variables are independent of each other and are the linear combination of original variables. Two models were developed: one for trained taste panel (TP) and one for slice shear force (SSF). Significant (p<0.10) correlations of individual textural features and/or the canonical variables were found with all of the biochemical traits that were measured. For example, the following biochemical traits were correlated to one or more of the image-textural features or canonical variables: Table 1 refers to classifications based on Taste Panel Ratings and Table 2 refers to correlations from Warner-Bratzler shear force.

TABLE 1

Correlations to Biological Properties of Textural Features Based on Tenderness Classification from Taste Panel Ratings

| Biological Property | Textural features extracted at key wavelength bands | | | Canonical variable |
|---|---|---|---|---|
| | Dissimilarity | Homogeneity | Correlation | |
| Muscle pH | | | | |
| Sarcomere length | 1057 | 1395 | | |
| Troponin-T degradation at day 2 | 1142 and 1280 | | | |
| Troponin-T degradation at day 14 | | | | Can1 |
| Fat % | 1057; 1091; 1115 | | 1115 | |
| Moisture % | 1057; 1091; 1115; 1280 | | | Can2 |
| Ash % | 1057; 1142; 1280 | | 1057; 1115 | |
| Protein % | 1057; 1091; 1115; 1142; 1280 | | | |

TABLE 2

Correlations to Biological Properties of Textural Features Based on Tenderness Classification from Warner-Bratzler Shear Force

| Biological Property | Textural features extracted at key wavelength bands (nm) | | | | | Canonical variables |
|---|---|---|---|---|---|---|
| | Dissimilarity | Homogeneity | Mean | Variance | Second Moment | |
| Muscle pH | | | | | | Can1 |
| Sarcomere length | 1057; 1280; 1395 | 1395 | 1091; 1115 | 1280 | | |
| Troponin-T degradation at day 14 | | | | | | Can1 |
| Fat % | 1057 | | | | | Can1 |
| Moisture % | 1280 | | | 1057; 1091;1280 | | Can1 |
| Ash % | 1057; 1280 | | 1091; 1115 | 1057; 1091; 1280 | | |
| Protein % | 1057; 1280 | | | | 1034 | |
| Insoluble collagen | | | | | | Can2 |
| Total collagen | | | | | | Can2 |

TABLE 3

Evaluation of multispectral imaging system for predicting SSF

| Reference | Actual | Predicted | Cross-validation Results |
|---|---|---|---|
| SSF | Tender | Tender | 156 |
| | Tender | Tough | 18 |
| | Tough | Tender | 6 |
| | Tough | Tough | 19 |
| | Overall accuracy | | 87.79% |

TABLE 4

Evaluation of multispectral imaging system for predicting TP

| Reference | Actual | Predicted | Cross-validation Results |
|---|---|---|---|
| TP | Tender | Tender | 97 |
| | Tender | Tough | 11 |
| | Tough | Tender | 6 |
| | Tough | Tough | 26 |
| | Overall accuracy | | 86.62% |

EXAMPLE 2

Evaluation of Eight Extracted Textural Features from Multispectral Images Captured at Key Wavelength Bands Eight textural features were extracted using gray level co-occurrence matrix (GLCM) analysis from each of 12 identified bands. Textural features can also be extracted by other methods such as Gabor filters and/or wavelet analysis from each of those identified bands. Thus, 96 features were extracted. In addition to textural features, marbling features such as number and distribution of fat flecks, marbling texture, and % fat area can also be extracted. A stepwise discriminant regression method was used to select 46 variables. These variables were used to classify the steaks into two tenderness categories. The overall accuracy was 88% for SSF and 87% for taste panel (TP). The results are presented in Table 3 for predicting SSF and Table 4 for TP below.

Other pattern recognition and machine learning algorithms like canonical discriminant analysis, neural networks, and fuzzy-logic approaches can be used to classify steaks into tenderness categories based on extracted textural features.

Often, the beef industry is interested in classifying steaks into two categories—tender and tough. The pattern recognition models can be easily modified to classify steaks into two categories. Similarly, if a company is interested in three or more categories, that can also be easily achieved.

Instead of classifying steaks into tenderness categories, pattern recognition models such as multiple linear regressions, non-linear regression, principal component regression, partial least squares regression, and similar methods may be used to predict the tenderness scores such as slice shear force, Warner-Bratzler shear force, or sensory scores.

EXAMPLE 3

Identification of Key Wavelength Bands for VNIR Multispectral Imaging System PCA was implemented to reduce the spectral dimension of a Region of Interest (ROI) within a hyperspectral image. The optimal number of PC images was chosen with Eigen values significantly greater than zero. (Johnson, R. A., 1998. Applied Multivariate Methods for Data Analysis. Duxbury Press, New York, N.Y.) For this step, the first five PC images had Eigen values significantly greater than zero. These Eigen values explained over 90% of the variance of all bands for the image. In this study, 'mosaic' data transformation was used.

FIG. 9 shows the first three loading vectors. By "peak-valley analysis", 12 key wavelengths can be identified.

Twelve key wavelength bands in the visible near-infrared (VNIR: 400-1000 nm) were identified. The wavelengths (455, 480, 520, 545, 568, 590, 604, 636, 722, 750, 814, and 850 nm) were identified as playing major roles in constructing the PC images (See FIG. 9). Multispectral images are preferably acquired only at the key wavelength bands, in the system and process of the invention, making it well-adapted for industrial implementation.

EXAMPLE 4

Identification of Key Wavelengths for Near-Infrared Multispectral Imaging System

Sample Collection

Beef ribeye steaks (*longissimus dorsi* muscle) between 12$^{th}$ and 13$^{th}$ ribs at 2 to 5-day post-mortem were collected from four different regional packing plants, vacuum packaged, and shipped to a central location. Before imaging, the samples were removed from their vacuum packages and were allowed to oxygenate for 30 minutes. Hyperspectral images of 229 beef ribeye steaks at 2 to 5-day post-mortem were then collected. Immediately after imaging, the samples were vacuum-packaged and aged until 14 days postmortem in these vacuum packages. After 14 days of aging, the samples were frozen to prevent further aging. Prior to tenderness measurements, the samples were thawed overnight at refrigerated temperatures in the cooler. The samples were then removed from the vacuum packages, allowed to oxygenate for 30 minutes, cooked in an impingement oven with a moving-belt, and slice shear force (SSF) values were recorded. The operations such as freezing, thawing, and cooking were applied equally to all samples and therefore should have had minimal effect on the accuracy of the model. Based on the SSF values, the samples were classified into three tenderness categories: tender (SSF≤205.80 N), intermediate (205.80 N<SSF<254.80 N), and tough (SSF≥254.80 N). These categories were used as references.

Image Preprocessing

During image acquisition, dark and white hyperspectral images were taken at 15 to 20-minute intervals. After correcting for bad pixels, reflectance image was calculated using Equation 1.

$$ReflectanceImage = \frac{RawImage - DarkImage}{WhiteImage - DarkImage}$$

After calculating reflectance, a Region-of-Interest (ROI) of size 150×300 pixels (56.3 mm×112.5 mm) near the center of the image was selected. No manual interaction was required to select the ROI. The ROI size was selected in such a way that the ROI fit within the ribeye area. Further image processing steps were performed on these ROI hyperspectral images. Out of the 229 beef samples, we used 156 beef samples to obtain loading vectors and 76 beef samples to evaluate the robustness and validity of loading vectors in predicting beef tenderness.

In this study, 'spectroscopic' data transformation was used. The dimensionality reduction technique 'PLS' was used for obtaining loading vectors.

Figure 7:
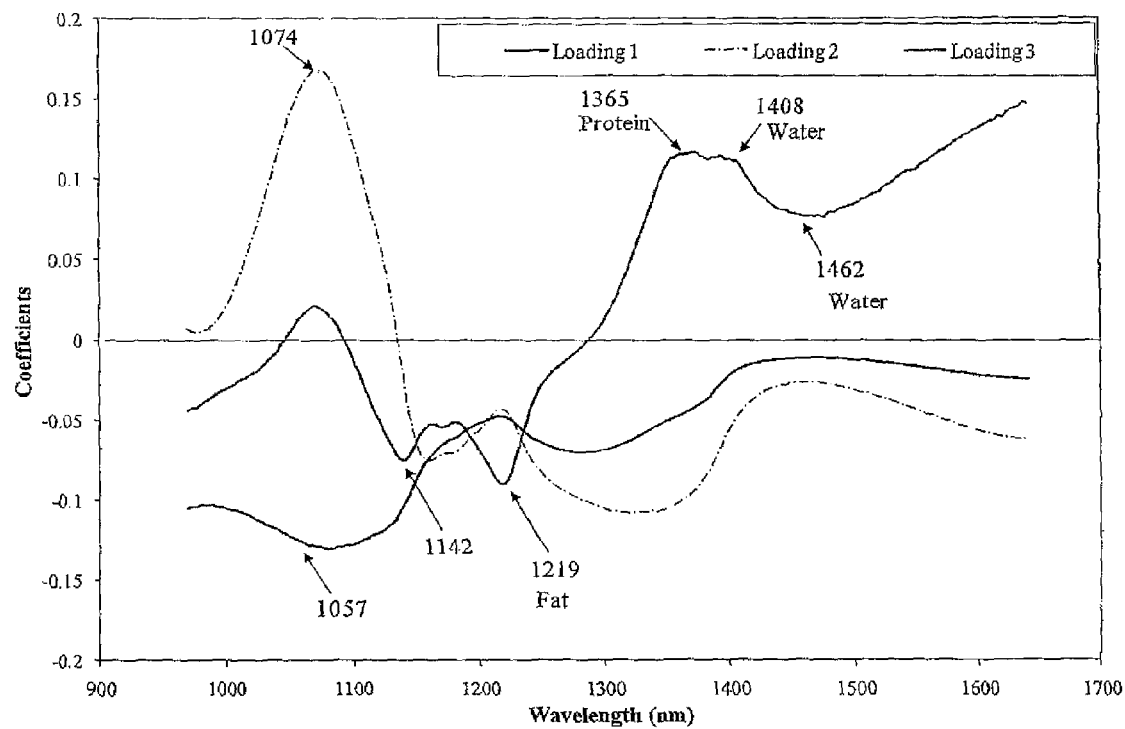
FIG. 7 and FIG. 8 are graphs plotting wavelengths vs. coefficients and depicting loading (Eigen) vectors from partial least squares regression (PLSR) for near-infrared wavelengths.

The peaks and valleys of the loading vectors identify key wavelengths. Hence, the wavelengths corresponding to the peaks and valleys of the loading vectors can be considered as key wavelengths—1057, 1074, 1091, 1115, 1142, 1176, 1219, 1280, 1365, 1395, 1408, and 1462 nm (FIGS. 7 & 8). It is possible to combine the identified wavelengths by using various arithmetic operations to remove additive and multiplicative errors. Among the twelve key wavelengths, absorption at 1219 nm was due to C—H second overtone; absorptions at 1365 and 1395 nm were due to C—H combination; and absorptions at 1408 and 1462 nm were due to O—H first overtone. Because the major constituents of beef are water, protein, and fat, it is possible to relate the vibrations (overtone and combination) to the constituents of beef. So by considering the chemical structures of water, fat, and protein and their vibrational behavior, it can be concluded that the absorptions at 1219 nm were primarily due to fat; absorptions at 1365 and 1395 nm were primarily due to protein; and absorptions at 1408 and 1462 nm were primarily due to water.

We claim:

1. A system and method for analyzing one or more properties of meat, comprising an image acquisition system and an image analysis system, which image acquisition system employs multispectral imaging of said meat at predetermined key wavelength bands and communicates said images to said image analysis system which extracts data from said image, processes it according to programs residing therein, and produces an output which comprises a conclusion about said one or more of said properties, wherein said image is acquired at a time ($t_0$) and said output is a forecast of the tenderness properties of said meat at a time ($t_1$) which is later in time than ($t_0$).

2. The system and method of claim 1, wherein said time ($t_1$) is the time when said meat will be available for preparation by a consumer.

3. The system and method of claim 1, wherein said image is acquired at a time ($t_0$) and said output is also used to make a prediction of the properties of said meat at said time ($t_0$).

4. The system and method of claim 1, wherein said number of predetermined wavelengths is from one to about twenty-five wavelengths.

5. The system and method of claim 4, wherein said number of predetermined wavelengths is from two to twelve wavelengths.

6. The system and method of claim 5, wherein said number of said predetermined wavelengths is four to eight wavelengths.

7. The system and method of claim 1, wherein said predetermined wavelengths are in the visible/near infrared (VNIR) region (400-1000 nm).

8. The system and method of claim 7, wherein said meat is beef and said wavelengths are selected from the group consisting of 455, 480, 520, 545, 568, 590, 604, 636, 722, 750, 814, and 850 nm and combinations thereof.

9. The system and method of claim 8, wherein each of said wavelengths can vary by ±20 nm.

10. The system and method of claim 1 wherein said predetermined wavelengths are in the NIR region (900-2500 nm).

11. The system and method of claim 10 wherein said meat is beef and, wherein said wavelengths are selected from the group consisting of 1057, 1074, 1091, 1115, 1142, 1176, 1219, 1280, 1365, 1395, 1408, and 1462 nm and combinations thereof.

12. The system and method of claim 10 wherein each of said wavelengths can vary by ±20 nm.

13. The system and method of claim 1, wherein at least one of said predetermined wavelengths is associated with fat properties and at least one wavelength is associated with protein properties of said meat.

14. The system and method of claim 1 wherein said meat is beef.

15. The system and method of claim 1 wherein said image analysis comprises correlating one or more image-textural features with tenderness of said raw meat, wherein said correlating comprises applying a pattern-recognition algorithm to said textural features.

16. The system and method of claim 15, wherein said image-textural features are correlated by performing at least one computation of statistical values based on said image.

17. The system and method of claim 16, wherein said computations are selected from the group consisting of a co-occurrence matrix analysis, a wavelet analysis, a covariogram analysis and an analysis utilizing Gabor filters.

18. The system and method of claim 15, wherein said image-textual features comprise one or more of a mean, a variance, a homogeneity, a contrast, a dissimilarity, an entropy, a second moment, a correlation, autocorrelation, skewness and kurtosis.

19. The system and method of claim 1 wherein said forecast of tenderness is associated with slice shear force values corresponding to cooked cuts of beef.

20. The system and method of claim 1, wherein said forecast of tenderness is associated with values selected from the group consisting of Warner-Bratzler shear force values, slice shear force values, sensory analysis and combinations thereof.

21. The system and method of claim 1, wherein said meat is beef, and wherein a multispectral image of the cross section of a ribeye muscle exposed from a carcass side is captured.

22. The system and method of claim 1, further comprising determining one or more additional properties of said beef from the same image simultaneously.

23. The system and method of claim 1, further comprising an equipment and sample stabilization means so that shaking of camera is minimized allowing good quality images to be acquired.

24. The system and method of claim 1, wherein an image acquisition means is comprises a camera, a wavelength dispersion unit, a lens, a light source and a housing.

25. The system and method of claim 24, wherein said wavelength dispersion unit is selected from spectrograph LCTF- and AOTF-based systems.

26. The system and method of claim 24, wherein said wavelength dispersion unit is a set of band-pass filters in a wheel, whereupon when the filter wheel is rotated a spectral band is collected.

27. A system and method for analyzing one or more properties of meat, comprising an image acquisition system and an image analysis system, which image acquisition system employs multispectral imaging of said meat at predetermined key wavelength bands and communicates said images to said image analysis system which extracts data from said image, processes it according to programs residing therein, and produces an output which comprises a conclusion about said one or more of said properties, wherein said image is acquired at a time ($t_0$) and said output is a forecast of one or more biological properties of said meat at a time ($t_1$) which is later in time than ($t_0$).

28. The system and method of claim 27, wherein said time ($t_1$) is the time when said meat will be available for preparation by a consumer.

29. The system and method of claim 27, wherein said image is acquired at a time ($t_0$) and said output is also a prediction of the properties of said meat at said time ($t_0$).

30. The system and method of claim 29, wherein said property is tenderness.

31. The system and method of claim 27, wherein said number of predetermined wavelengths is from one to about twenty-five wavelengths.

32. The system and method of claim 31, wherein said number of predetermined wavelengths is from two to twelve wavelengths.

33. The system and method of claim 32, wherein said number of said predetermined wavelengths is four to eight wavelengths.

34. The system and method of claim 27, wherein said predetermined wavelengths are in the visible/near infrared (VNIR) region (400-1000 nm).

35. The system and method of claim 34, wherein said meat is beef and said wavelengths are selected from the group consisting of 455, 480, 520, 545, 568, 590, 604, 636, 722, 750, 814, and 850 nm and combinations thereof.

36. The system and method of claim 35, wherein each of said wavelengths can vary by ±20 nm.

37. The system and method of claim 27, wherein said predetermined wavelengths are in the NIR region (900-2500 nm).

38. The system and method of claim 37, wherein said meat is beef and, wherein said wavelengths are selected from the group consisting of 1057, 1074, 1091, 1115, 1142, 1176, 1219, 1280, 1365, 1395, 1408, and 1462 nm and combinations thereof.

39. The system and method of claim 37, wherein each of said wavelengths can vary by ±20 nm.

40. The system and method of claim 27, wherein at least one of said predetermined wavelengths is associated with fat properties and at least one wavelength is associated with protein properties of said meat.

41. The system and method of claim 40, wherein said meat is beef.

42. The system and method of claim 27, wherein said image analysis comprises correlating one or more image-textural features with tenderness of said raw meat, wherein said correlating comprises applying a pattern-recognition algorithm to said textural features.

43. The system and method of claim 42, wherein said image-textural features are correlated by performing at least one computation of statistical values based on said image.

44. The system and method of claim 43, wherein said computations are selected from the group consisting of a co-occurrence matrix analysis, a wavelet analysis, a covariogram analysis and an analysis utilizing Gabor filters.

45. The system and method of claim 42, wherein said image-textual features comprise one or more of a mean, a variance, a homogeneity, a contrast, a dissimilarity, an entropy, a second moment, a correlation, autocorrelation, skewness and kurtosis.

46. The system and method of claim 27, wherein said meat is beef, and wherein a multispectral image of the cross section of a ribeye muscle exposed from a carcass side is captured.

47. The system and method of claim 27, further comprising determining one or more additional properties of said beef from the same image simultaneously.

48. The system and method of claim 27, further comprising an equipment and sample stabilization means so that shaking of camera is minimized allowing good quality images to be acquired.

49. The system and method of claim 27, wherein an image acquisition means is comprises a camera, a wavelength dispersion unit, a lens, a light source and a housing.

50. The system and method of claim 49, wherein said wavelength dispersion unit is selected from spectrograph LCTF- and AOTF-based systems.

51. The system and method of claim 49, wherein said wavelength dispersion unit is a set of band-pass filters in a wheel, whereupon when the filter wheel is rotated a spectral band is collected.

* * * * *

UNITED STATES PATENT AND TRADEMARK OFFICE
CERTIFICATE OF CORRECTION

Page 1 of 1

PATENT NO. : 8,774,469 B2
APPLICATION NO. : 13/143897
DATED : July 8, 2014
INVENTOR(S) : Subbiah et al.

It is certified that error appears in the above-identified patent and that said Letters Patent is hereby corrected as shown below:

In the Specification
Col. 3, line 59, replace "Serial Number 035080" with -- Serial Number 12/035080 --
Col. 15, line 11, replace "number opf spectra" with -- number of spectra --

In the Claims
Col. 21, Claim 24, line 2, delete "is" before "comprises."
Col. 23, Claim 49, line 2, delete "is" before "comprises."

Signed and Sealed this
Seventh Day of October, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,774,469 B2 | Page 1 of 1 |
| APPLICATION NO. | : 13/143897 | |
| DATED | : July 8, 2014 | |
| INVENTOR(S) | : Subbiah et al. | |

It is certified that error appears in the above-identified patent and that said Letters Patent is hereby corrected as shown below:

In the Specification
Col. 3, line 59, replace "Serial Number 035080" with -- Serial Number 12/035080 --
Col. 15, line 11, replace "number opf spectra" with -- number of spectra --

In the Claims
Col. 21, Claim 24, line 63, delete "is" before "comprises."
Col. 23, Claim 49, line 21, delete "is" before "comprises."

This certificate supersedes the Certificate of Correction issued October 7, 2014.

Signed and Sealed this
Eleventh Day of November, 2014

Michelle K. Lee
*Deputy Director of the United States Patent and Trademark Office*